United States Patent
Przepasniak et al.

(10) Patent No.: US 7,138,560 B2
(45) Date of Patent: Nov. 21, 2006

(54) ABSORBENT ARTICLE WITH TIME-DELAYED ABSORBENT BINDER COMPOSITION

(75) Inventors: Ann Marie Przepasniak, Appleton, WI (US); Dave A. Soerens, Neenah, WI (US); Russell P. George, Appleton, WI (US); William Reeves, Appleton, WI (US); Tina J. Flaherty, Larsen, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 54 days.

(21) Appl. No.: 10/732,163

(22) Filed: Dec. 10, 2003

(65) Prior Publication Data

US 2005/0131362 A1      Jun. 16, 2005

(51) Int. Cl.
*A61F 13/15* (2006.01)
(52) U.S. Cl. ..................................................... 604/364
(58) Field of Classification Search ................ 604/364
See application file for complete search history.

(56) References Cited

U.S. PATENT DOCUMENTS

| | | | |
|---|---|---|---|
| 3,420,235 A | 1/1969 | Harmon | |
| 3,726,277 A | 4/1973 | Hirschman | |
| 3,891,584 A | 6/1975 | Ray-Chaudhuri et al. | |
| 3,983,873 A | 10/1976 | Hirschman | |
| 4,175,561 A | 11/1979 | Hirschman | |
| 4,341,217 A | 7/1982 | Ferguson et al. | |
| 4,522,967 A | 6/1985 | Sheldon et al. | |
| 4,600,404 A | 7/1986 | Sheldon et al. | |
| 5,429,631 A | 7/1995 | Grenier | |
| 5,460,624 A | 10/1995 | Ahr et al. | |
| 5,484,429 A | 1/1996 | Vukos et al. | |
| 5,509,913 A | 4/1996 | Yeo | |
| 5,573,523 A | 11/1996 | Whalen et al. | |
| 5,605,764 A * | 2/1997 | Miller et al. | 428/480 |
| 5,613,964 A * | 3/1997 | Grenier | 604/385.01 |
| 5,681,299 A | 10/1997 | Brown | |
| 5,693,707 A * | 12/1997 | Cheng et al. | 524/556 |
| 5,762,644 A | 6/1998 | Osborn, III et al. | |
| 5,891,126 A | 4/1999 | Osborn, III et al. | |
| 5,948,710 A | 9/1999 | Pomplun et al. | |
| 5,952,251 A | 9/1999 | Jackson et al. | |
| 6,033,391 A | 3/2000 | Osborn, III et al. | |
| 6,063,858 A * | 5/2000 | Daniels et al. | 524/563 |
| 6,171,292 B1 | 1/2001 | Osborn, III et al. | |
| 6,183,456 B1 | 2/2001 | Brown et al. | |

(Continued)

FOREIGN PATENT DOCUMENTS

EP          0161663          11/1985

(Continued)

OTHER PUBLICATIONS

U.S. Appl. No. 10/732,827, filed Dec. 10, 2003.

*Primary Examiner*—Tatyana Zalukaeva
*Assistant Examiner*—Ginger T. Chapman
(74) *Attorney, Agent, or Firm*—Dority & Manning (57) ABSTRACT

A personal care absorbent article includes a generally liquid permeable cover sheet, a generally liquid impermeable baffle, and an absorbent material disposed between the cover sheet and the baffle. A water soluble flexible absorbent binder composition is applied between the cover sheet and the baffle and functions as a primary absorbent material and to adhere the cover sheet to the baffle. The absorbent binder composition includes a crosslinked absorbent polymer and a polymer dispersion added in an amount so as to maintain structural integrity of the article for a time period of at least about two hours after the article is immersed in water by being flushed.

22 Claims, 4 Drawing Sheets

U.S. PATENT DOCUMENTS

| | | |
|---|---|---|
| 6,203,512 B1 | 3/2001 | Farris et al. |
| 6,270,486 B1 | 8/2001 | Brown et al. |
| 6,514,602 B1 | 2/2003 | Zhao et al. |
| 2001/0000796 A1 | 5/2001 | Osborn et al. |
| 2001/0001815 A1 | 5/2001 | Osborn et al. |
| 2001/0025163 A1 | 9/2001 | Brown et al. |
| 2002/0058921 A1 | 5/2002 | Sigl |
| 2003/0225388 A1 | 12/2003 | Bhavani |
| 2004/0018366 A1 | 1/2004 | George et al. |
| 2004/0019168 A1 | 1/2004 | Soerens et al. |
| 2004/0043688 A1 | 3/2004 | Soerens et al. |
| 2004/0122402 A1 | 6/2004 | McDaniel |
| 2004/0122403 A1 | 6/2004 | Mtichler |

FOREIGN PATENT DOCUMENTS

| | | |
|---|---|---|
| EP | 0781538 | 7/1997 |
| EP | 0835337 | 10/2001 |
| EP | 0989837 | 4/2002 |
| WO | 9518191 | 7/1995 |
| WO | 9808475 | 3/1998 |
| WO | 9926574 | 6/1999 |
| WO | 9956689 | 11/1999 |
| WO | 0166160 | 9/2001 |
| WO | 2004 011046 A1 | 2/2004 |
| WO | 2004 060248 A1 | 7/2004 |

\* cited by examiner

ABSORBENT ARTICLE WITH TIME-DELAYED ABSORBENT BINDER COMPOSITION

FIELD OF THE INVENTION

The present invention relates to the field personal care absorbent articles, with particular application to feminine hygiene products.

BACKGROUND

A broad range and wide variety of absorbent articles configured for absorption of bodily exudates such as menstrual fluid are well known. Such products include, for example, diapers, adult incontinence products, feminine hygiene products, and so forth. With respect to feminine hygiene, the art has offered two basic types of protection: namely sanitary napkins and panty liners, developed for external wear about the pudendum region, and tampons, developed for placement within the vaginal cavity, and accordingly for interruption of menstrual flow therefrom prior to such menstrual flow reaching the vestibule. Hybrid feminine hygiene protection devices, attempting to merge the structural features of both sanitary napkins and tampons in a single type of device, have also been proposed, but have not seen a meaningful measure of acceptance.

Other less intrusive devices, known as labial or interlabial devices or pads, have also been proposed. These articles are designed to reside primarily within the wearer's vestibule while having a portion residing at least partially external of the wearer's vestibule. Interlabial articles can provide a preferred profile of appearance when viewed through a wearer's outer garments and do not have the same problem of reliance on swelling within the vaginal canal as required by tampons. U.S. Pat. Nos. 5,484,429; 4,175,561; 3,983,873; and 3,726,277 disclose various types of interlabial absorbent articles.

Interlabial absorbent articles are generally designed to be expelled by the urine stream when the wearer urinates. The article thus falls into a conventional toilet where it can be flushed. The relatively small size of interlabial devices facilitates flushing in conventional sewer and septic systems. However, care must still be taken that the articles disperse in the sewer or septic system so as not to obstruct or otherwise damage the system. In this regard, efforts have been made in the art to provide interlabial articles that dissipate or disperse quickly in water. For example, U.S. Pat. No. 6,171,292 B1 describes an interlabial absorbent article that is designed so that the components of the article fragment within at least two hours of exposure to mildly agitated room temperature water. Alternately, the components may separate from each other without themselves fragmenting. The '292 patent teaches that it would be most preferred if the article fragmented within about 15 minutes.

U.S. Pat. No. 5,573,523 describes a biodegradable and flushable mini-pad formed entirely of cellulosic materials. The outer panels are mechanically bonded at their perimeters without an adhesive to enhance biodegradation of the pad.

However, the desire for an interlabial absorbent article that disperses quickly in water may conflict with performance requirements for the article. Due to the relatively high water content of viscous and vaginal fluids, use of a water soluble adhesive (or no adhesive at all) that immediately starts to dissolve and cause the article to break up could sacrifice the seal strength and product integrity while in use. Wearing time of the product may also be reduced if the article tends to break apart prior to being expelled upon urination as intended. Absorbent articles that tend to fragment into individual components before or during flushing may also tend to cause clogging of a structure's plumbing system. The more components or articles that "travel" through a home's contorted plumbing system per absorbent article flushed increases the risk that any one such component may become entrapped or entangled on roots or the like, as compared to a single intact article.

Thus, a need exists for an absorbent article design, including an interlabial absorbent article, that offers the benefits of a dispersible product without sacrificing performance of the article or adding to the risk of plumbing clogs or other problems upon flushing the article.

SUMMARY

Objects and advantages of the invention will be set forth in part in the following description, or may be obvious from the description, or may be learned through practice of the invention.

Although the present invention has particular usefulness in the field of feminine care articles such as interlabial devices, it should be appreciated that any manner of personal care absorbent article may benefit from the invention, including incontinence articles, and the like. All such uses are within the scope and spirit of the invention. For ease of description only, the working environment of the invention is assumed to be feminine care interlabial absorbent articles.

The present invention relates to a unique configuration particularly suited for a feminine care interlabial absorbent article that offers distinct advantages over conventional devices. The interlabial absorbent article includes a generally liquid permeable cover sheet, a generally liquid impervious "baffle" or back sheet, and a flexible absorbent binder composition applied between the cover sheet and the baffle. The absorbent binder composition may be applied as a coating and serves as a fluid storage (absorbent) layer and also bonds the cover sheet to the baffle. In particular embodiments, the article may contain additional materials, such as an additional layer of absorbent material to add supplemental absorbent capacity. Any conventional absorbent material may be used for this purpose.

The article is formed by applying the absorbent binder composition to one or both of the facing surfaces of the cover sheet and baffle, pressing the sheets together, and crosslinking the absorbent binder composition to form the flexible absorbent binder layer. If an additional layer, such as an absorbent material layer, is provided, the absorbent binder composition may also be applied to one or both of the sides thereof. Because the flexible absorbent binder composition is crosslinked while the composition is in contact with the other layers, the composition serves both as an absorbent layer and an adhesive (binder) layer, and may eliminate the need for additional adhesive or bonding steps. However, in alternate embodiments, such additional adhesive or bonding steps may be desired to achieve a desired degree of product integrity such that the article reaches a particular location in the septic system or municipal waste treatment plant prior to breaking apart.

The absorbent binder composition includes a generally water soluble absorbent polymer component and a polymer dispersion agent added to the composition prior to crosslinking in an amount such that the crosslinked composition maintains structural integrity of the article for a time period of at least about two hours after the article is immersed in water by being flushed. Desirably, the polymer agent is present in an amount such that the article looses structural integrity within about 24–72 hours after immersion. The polymer dispersion may be one or a combination of widely recognized binding agents, such as a latex, cellulose ester, and the like.

In particular embodiments, the absorbent polymer component of the composition may be a water-soluble ionic polymer capable of sufficient non-radiative crosslinking within about 10 minutes at a temperature not more than about 120° C. The polymer reaches an absorbent capacity of at least one gram per gram using the centrifuge retention capacity test, as described herein. For example, the absorbent polymer may comprise about 15 to about 99.9% by mass monoethylenically unsaturated polymer units, about 0.1 to about 20% by mass ester units selected from the group consisting of acrylate and methacrylate ester units that include an alkoxysilane functionality, and about 0.1 to about 75% by mass of units selected from the group consisting of polyolefin glycol and polyolefin oxide units.

The absorbent binder composition may be applied as a coating using conventional techniques, such as a spraying, in a variety of patterns. For example, the composition may be applied as a generally continuous coating with uniform thickness over the entire surface area of one or both of the cover sheet and baffle. In alternate embodiments, particular regions may be coated with different variations of the binder composition. For example, in one embodiment, a circumferential edge region or border of the cover sheet and baffle may be coated with binder composition having a greater percentage of the polymer dispersion as compared to a central region, the circumferential edge region thus providing an enhanced seal with decreased absorbent capacity. Similarly, a central region of the article may contain the absorbent binder composition having a greater percentage of the absorbent polymer as compared to circumferential edge regions.

In an alternate embodiment, the article may be provided with a generally central longitudinally disposed region between the cover sheet and the top sheet that is uncoated with the absorbent binder composition. This uncoated region would define an area of structural weakness that may be used as a fold line for the article.

The present invention also includes various embodiments of a method for forming an interlabial absorbent article that is dispersible in water after at least about two hours.

Aspects of the invention will be described in greater detail below by reference to embodiments illustrated in the attached drawings.

DETAILED DESCRIPTION

Reference will now be made in detail to embodiments of the invention, one or more examples of which are illustrated in the drawings. Each embodiment and example are provided for purposes of explaining the invention, and are not meant as a limitation of the invention. For example, features illustrated or described as part of one embodiment may be used with another embodiment to yield still a further embodiment. It is intended that the present invention include these and other modifications and variations as come within the scope and spirit of the invention.

As used herein the term "dispersible" means that the fibers of a material or components of an article are capable of debonding, resulting in the material or article breaking down into smaller pieces than the original sheet or article. Debonding is generally a physical change of scattering or separation, as compared to a state change, such as dissolving, wherein the material goes into solution, e.g., a water soluble polymer dissolving in water.

As used herein, the term "flushable" means that an article, when flushed down a conventional commode containing approximately room temperature water, will pass through the commode plumbing, the sewer lateral (i.e., the piping between the house or building and the main sewer line) without clogging.

As used herein, the term "water dispersible" refers to a fibrous nonwoven composite structure which when placed in an aqueous environment will, with sufficient time, break apart into smaller pieces. As a result, the structure once dispersed may be more advantageously processable in recycling processes or flushable in, for example, septic and municipal sewage treatment systems. If desired, such fibrous nonwoven structures may be made more water-dispersible or dispersion may be hastened by the use of agitation and/or certain triggering means.

As used herein, the term "water soluble" refers to a state change of a material or composition when exposed to an aqueous environment, such as dissolving, wherein the material goes into solution, e.g., a water soluble polymer dissolving in water.

As used herein, the term "interlabial absorbent article" refers to a device having at least one absorbent component, and which is specifically configured for disposition between the labia majora, extending at least partially into the vestibule of a female wearer during use. The vestibule is considered to be the region defined within the labia beginning at about a point lying caudally from the anterior labial commissure and extending rearward to the posterior labial commissure, and bounded inwardly by the floor of the vestibule. One of skill in the art fully understands that there is a wide range of variation among women with respect to the relative size and shape of labia majora and labia minora as the same interrelatedly define the contour of the vestibule. For purposes of the present description, however, such differences will not specifically be addressed, it being recognized that in any event the disposition of the absorbent article into the vestibule necessitates placement between the labia majora regardless of any such consideration respecting the labia minora.

An interlabial absorbent article is disposed at least partially within the vestibule for partially occluding the vestibule with respect to fluid flow from the vestibule. In this regard, the predominant use of the absorbent article is for the absorption of menstrual or intermenstrual fluid emitted via the vaginal orifice, although the article is equally well adapted to serve as a type of incontinence device for absorption of urine as occurs upon minor, female incontinence.

"Binder" or "binding agent" includes materials which are capable of attaching themselves to a substrate or are capable of attaching other substances to a substrate.

"Knife over roll coating" refers to a process in which a knife is positioned, with a specified gap, above a substrate that is moving beneath the knife on a moving roll. In this manner, the knife spreads a specified thickness of coating material onto the substrate.

"Nonwoven" or "nonwoven web" refers to materials and webs or material having a structure of individual fibers or filaments which are interlaid, but not in an identifiable manner as in a knitted fabric. The terms "fiber" and "filament" are used interchangeably. Nonwoven fabrics or webs have been formed from many processes such as, for example, meltblowing processes, spunbonding processes, air laying processes, and bonded carded web processes. The basis weight of nonwoven fabrics is usually expressed in ounces of material per square yard (osy) or grams per square meter (gsm) and the fiber diameters are usually expressed in microns. (Note that to convert from osy to gsm, multiply osy by 33.91.)

"Roll printing" or "roll coating" refers to a process in which the application of a deposited material, generally as a paste, onto a substrate is carried out by transferring the deposited material from a roll onto the substrate in a more or less uniform layer using one or more rolls, which may be engraved, and a pool cylinder. A doctor blade is used to scrape any excess deposited material from the rolls or substrate. The doctor blade may be flat or have a patterned edge such as slots or ridges.

"Rotary screen printing" or "rotary screen coating" refers to a process that is a combination of roll printing or coating and screen printing or coating.

"Screen printing" or "screen coating" refers to a method of applying a deposited material by forcing the material to be deposited through a screen that may have uniform openings or patterned openings.

"Superabsorbent" refers to a water-swellable, water-insoluble organic or inorganic material capable, under the most favorable conditions, of absorbing at least about 15 times its weight and, more desirably, at least about 25 times its weight in an aqueous solution containing 0.9 weight percent sodium chloride. The superabsorbent materials can be natural, synthetic, and modified natural polymers and materials. In addition, the superabsorbent materials can be inorganic materials, such as silica gels, or organic compounds such as cross-linked polymers.

In one embodiment, the present invention provides an interlabial absorbent article configured for disposition primarily within the vestibule of a female wearer. The invention is not restricted to interlabial articles, and the benefits of the invention may be incorporated with various types and styles of absorbent articles in general. The article may take on any suitable overall shape and configuration, it being understood that the illustrated embodiments are for explanation purposes only. The article includes a liquid permeable cover sheet, a generally liquid impermeable baffle, and a coating of an absorbent binder composition applied to one or both of the facing surfaces of the baffle and cover sheet. The absorbent binder composition serves the purpose of forming a highly absorbent layer while adhering the various components of the article together. The absorbent binder composition provides sufficient absorbent capacity such that the conventional absorbent material layer provided with traditional interlabial articles may be dispensed with. However, it is within the scope and spirit of the invention to include a supplemental layer of absorbent material to supplement the absorbent capacity of the binder composition. In either case, the interlabial article according to the invention is significantly reduced in thickness, resulting in a slimmer and more comfortable device without sacrificing performance. The various components of the article are described in greater detail below.

The absorbent binder composition, alone or in combination with a supplemental seal, adheres the article components together such that after about two hours or more of mildly agitated exposure to room temperature water, the article looses structural integrity such that it disperses or breaks-up into at least two components. For example, the cover sheet may be completely removed from the baffle and, if provided, the supplemental absorbent material layer. The article is also considered to have lost structural integrity if the seal between the cover sheet and baffle opens or separates enough so that any supplemental absorbent material may disperse out from between the sheets. Thus, the sheets may still be at least partially attached. It is also within the scope and spirit of the invention that the individual components are also dispersible. For example, any one or combination of the cover sheet, baffle, absorbent binder composition, and supplemental absorbent material may be water dispersible. The individual components may also be biodegradable.

Various advantages may be achieved with an interlabial absorbent article according to the invention. For example, the product may be used for an extended period under conditions where it is exposed to bodily fluids having a high water content without worry that the product will prematurely fail either by coming apart or causing premature leakage because of poor product integrity. The article will eventually disperse in, or before, it reaches a municipal water sewage treatment plant. The article will be conveyed after flushing through a structure's plumbing system as a single component, thus minimizing the chance of clogging that exists with multiple components flowing through the system. If the product does become clogged as a single unit, it will eventually disperse and may become unclogged.

Referring to the figures in general, various embodiments of an interlabial absorbent article 10 are illustrated. The absorbent article 10 includes the cover sheet 12, baffle 14, and an absorbent binder composition 22 applied to one or both of the facing surfaces of the baffle 14 and cover sheet 12. The article 10 should be of a suitable size and shape which allows at least a portion, preferably a major portion, of the absorbent article to be disposed within the vestibule of a female wearer. In addition, the absorbent article 10 desirably at least partially occludes and intercepts the flow of menstrual fluid, urine or other bodily exudates from the wearer's vaginal orifice and/or urethral orifice.

The article 10 is not limited to any particular shape or configuration. In the illustrated embodiments, for example, the article 10 has an overall "butterfly" shape (oval with lateral tab or wing portions 20). One skilled in the art will readily appreciate, however, that other geometries may also be suitable, including, for example, rectangular, ovoid-like, elliptical, trapezoidal, circular-like, triangular, square-shaped, teardrop-shaped, diamond-shaped, butterfly, pear-shaped, heart-shaped or a variety of combinations thereof. In addition, tabs or wings may be used with any of the overall geometries.

The fluid permeable cover sheet 12 has an outwardly facing surfaces that may contact the body of the wearer and receive bodily exudate(s). The cover sheet 12 desirably is made of a material which is flexible and non-irritating to the tissues within the vestibule of a female wearer. As used herein, the term "flexible" is intended to refer to materials which are compliant and readily conform to the bodily surface(s) with which such materials are in contact, or materials which respond by easily deforming in the presence of external forces.

The cover sheet 12 is provided for comfort and conformability and functions to direct bodily exudate(s) away from the body, through the cover sheet 12 and toward the absorbent binder composition 22 and supplemental absorbent material 18 if provided. The cover sheet 12 should retain little or no liquid in its structure so that the cover provides a relatively comfortable and non-irritating surface next to the tissues within the vestibule of a female wearer. The cover sheet 12 can be constructed of any woven or nonwoven material which is easily penetrated by bodily fluids which contact the surface of the cover. Examples of suitable cover materials include cotton, rayon, bonded carded webs of polyester, polypropylene, polyethylene, nylon, or other heat-bondable fibers, polyolefins, such as copolymers of polypropylene and polyethylene, linear low-density polyethylene, and aliphatic esters such as polylactic acid. Finely perforated film webs and net material can also be used. A specific example of a suitable cover material is a bonded carded web made of polypropylene and polyethylene such as that used as cover stock for KOTEX® pantiliners and obtainable from Sandler Corporation, Germany. Other examples of suitable materials are composite materials of polymer and nonwoven fabric materials. The composite materials are typically in the form of integral sheets generally formed by the extrusion of a polymer onto a web of spunbonded material. The fluid permeable cover 12 can also contain a plurality of apertures (not shown) formed therein which are intended to increase the rate at which bodily fluid(s) can penetrate through the cover.

A physiologically hydrous cover sheet material is also suitable for use. As used herein, the phrase "physiologically hydrous" is intended to connote a sheet material which maintains a suitably moist interface between the tissues of the vestibule and the absorbent article 10 when disposed in the vestibular environment; material which is benign respecting the requirements of comfort associated with the interposition of fabric or fabric-like structures within the moist tissue environment of the vestibule, also considering that the absorbent article receives bodily fluid(s) migrating through the vestibule and conducts such fluids to the absorbent binder composition 22. Thus, while the cover sheet 12 is not "hydrous" in the classic sense prior to use, inasmuch as the sheet is dry at that time, the cover sheet 12 maintains, or at least does not interfere with the maintenance of, the proper moisture level or moisture balance required within the vestibule for proper maintenance of tissue health within the vestibule.

At least a portion of the surface of the cover sheet 12 can be treated with a surfactant in order to render the cover more hydrophilic. This results in permitting the insulting bodily fluid(s) to more readily penetrate the material The surfactant can also diminish the likelihood that the insulting bodily fluid(s), such as menstrual fluid, will flow off the cover sheet 12 rather than passing through the cover. One suitable approach provides for the surfactant to be substantially evenly distributed across at least a portion of the upper surface of the cover sheet 12 which overlies the layer of absorbent binder composition 22.

In an alternate embodiment, a light coating of the absorbent binder composition 22 may be applied to the cover sheet 12 to enhance the hydrous nature of the material prior to use.

The cover sheet 12 may also be embossed with any desired embossing pattern. Embossing techniques are well known to those skilled in the art. An embossing pattern not only creates an aesthetically pleasing surface, but the resulting embossed channels facilitate intake of menses fluid. Menses will tend to flow along the densified edges of the channels rather than pool on contact points of the cover sheet 12.

The baffle 14 can be constructed from any desired material which may be generally liquid-impermeable (although not required). Desirably, the baffle 14 permits passage of air and moisture vapor out of the absorbent 10 while blocking passage of bodily fluid(s). An example of a suitable material is a micro-embossed, polymeric film, such as polyethylene, polypropylene or polyester, having a minimum thickness of no less than about 0.025 mm and a maximum thickness of no greater than about 0.13 mm. Bicomponent films can also be used, as well as woven and nonwoven fabrics which have been treated to render such fabrics liquid-impermeable. An example of another suitable material is a closed cell polyolefin foam, for example, a closed cell polyethylene foam. A specific example of a baffle material is a polyethylene film such as that used in KOTEX® pantiliners and obtainable from Pliant Corporation, Schaumburg, Ill., USA.

Figure 3:
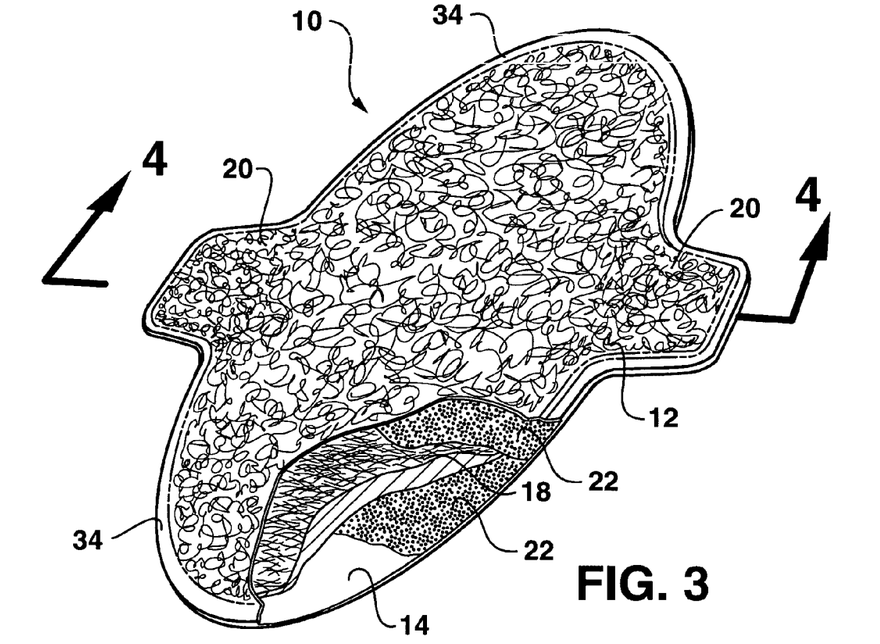
FIG. 3 is a perspective and partial cut-away view of an alternate embodiment of an interlabial absorbent article in accordance with the invention.

As mentioned, embodiments of the article 10 may include a supplemental layer of absorbent material 18, as depicted in FIG. 3. Because this layer 18 is not the primary absorbent means for the article 10, it may have a significantly reduced thickness or absorbent capacity as compared to the absorbent material layer(s) used in conventional interlabial devices. The supplemental absorbent material layer 18 can include any material capable of absorbing and/or adsorbing and thereafter retaining the intended bodily exudate(s), or temporarily taking in the bodily exudates followed by subsequent absorption by the absorbent composition. Suitable materials are also generally hydrophilic, compressible and conformable. The absorbent material 18 can be formed from any of the materials well known to those of ordinary skill in the art. Examples of such materials include, but are not limited to, various natural or synthetic fibers, multiple plies of creped cellulose wadding, fluffed cellulose fibers, rayon or other regenerated cellulose materials, wood pulp fibers or comminuted wood pulp fibers, airlaid material, textile fibers, a blend of polyester fibers and polypropylene fibers, absorbent foams, absorbent sponges, superabsorbent polymers, coated superabsorbent polymers, fibrous bundles or nits, or any equivalent material or combination of materials. Hydrophobic materials are also suitable for use where the hydrophobic material has been rendered hydrophilic according to any of a number of known methods for so doing. For example, the layer 18 may also be coated with the absorbent binder composition 22.

The supplemental absorbent material 18 desirably also has a relatively low density which is desirable for comfort. Generally, the absorbent material 18 has a density that can range up to about 0.5 g/cc; although the approximate density of the absorbent can vary according to, inter alia, the general design and intended disposition of the absorbent article 10 within the vestibule of a female wearer.

The supplemental absorbent material 18 can have a basis weight of about 600 gsm or less; with a preferred basis weight of about 50 to about 400 gsm; although the approximate basis weight of the absorbent can vary according to, inter alia, the general design and intended disposition of the absorbent article 10 within the vestibule of a female wearer.

A specific example of a suitable supplemental absorbent material is a coform material made of a blend of polypropylene and cellulose fibers such as that used in KOTEX® pantiliners and obtainable from Kimberly-Clark Corporation, Neenah, Wis., USA.

In a particular embodiment of the article 10 in accordance with the invention, the supplemental absorbent material 18 is dispersible in water. Cellulosic fiber webs are generally considered dispersible in water in that they readily fragment into individual fibers upon sufficient exposure to an aqueous environment. Various other water dispersible absorbent materials are known to those skilled in the art and may be used with the present invention. For example, U.S. Pat. Nos. 5,952,251 and 5,948,710, such patents incorporated herein by reference for all purposes, describe absorbent dispersible coform materials that may be suitable for the present invention. U.S. Pat. Nos. 6,171,292 B1 and 6,270,486 B1, incorporated herein by reference for all purposes, also disclose a number of dispersible absorbent materials that may be used with the present invention.

Figure 1:
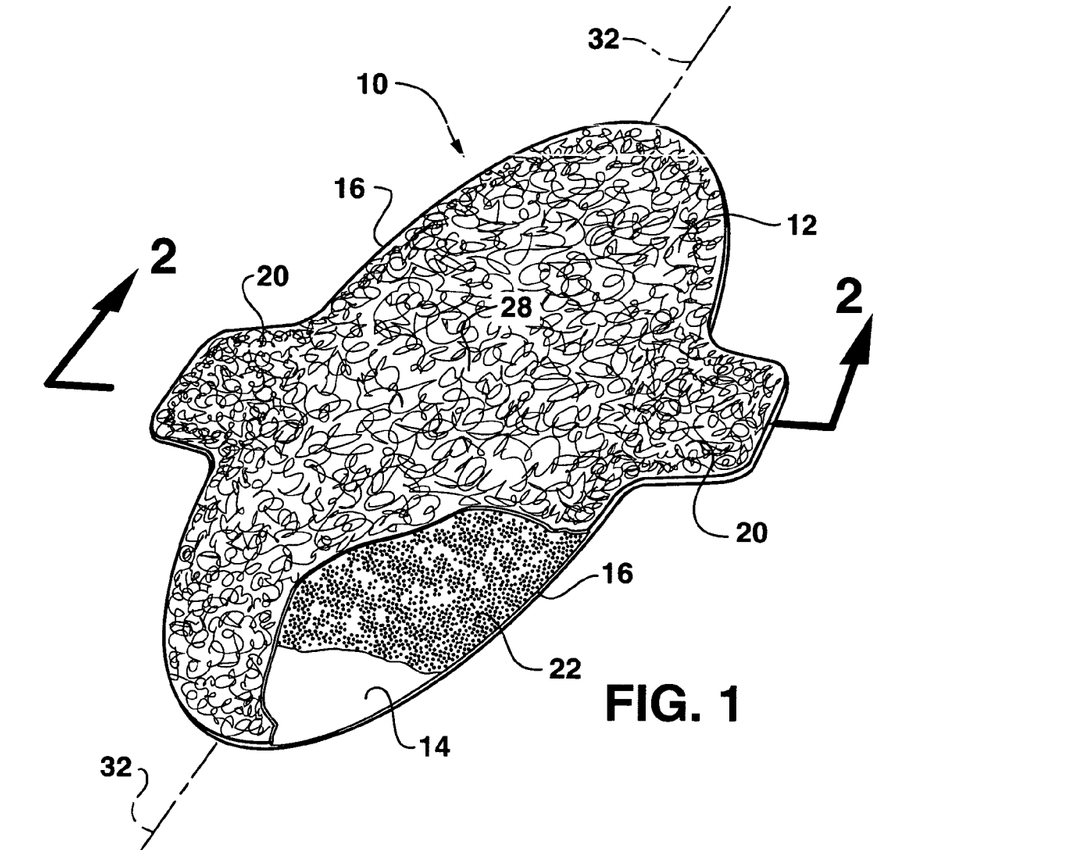
FIG. 1 is a perspective and partial cut-away view of an interlabial absorbent article in accordance with the invention.
Figure 2:
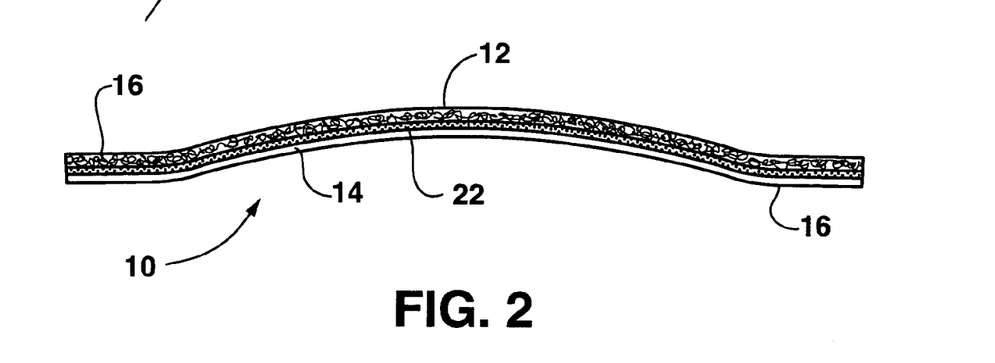
FIG. 2 is a cross-sectional view of the article of FIG. 1 taken along the lines indicated.
Figure 4:
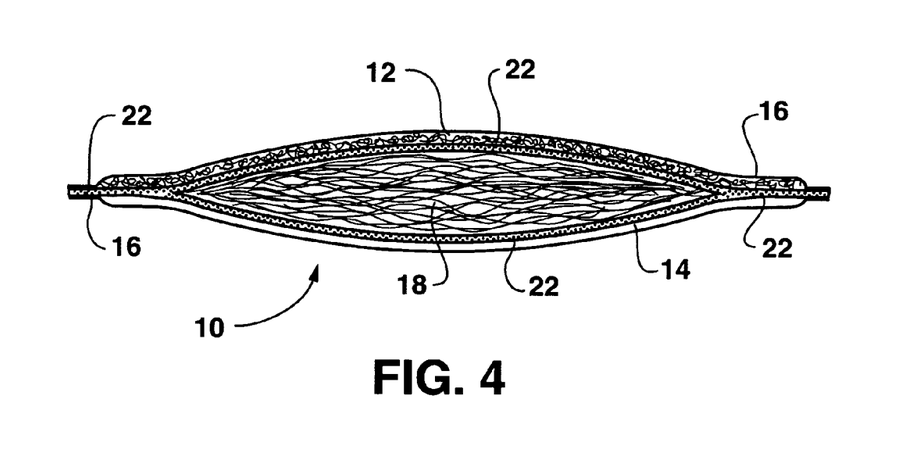
FIG. 4 is a cross-sectional view of the embodiment of FIG. 3 taken along the lines indicated.

The absorbent binder composition 22 may be applied to one or both of the facing surfaces of the cover sheet 12 and the baffle 14 such that, once crosslinked, the composition forms a thin flexible absorbent layer between the cover sheet 12 and baffle 14, as depicted in FIGS. 1 and 2. For the embodiment of FIGS. 3 and 4, the absorbent binder composition 22 is applied to the inner faces of the cover sheet 12 and baffle 14 so as to adhere the supplemental absorbent material layer 18 to both of the sheets. The binder composition 22 may be applied to the sheets 12, 14 during the manufacturing process of the articles 10. The binder composition 22 is suitably present in any concentration that provides a viscosity suitable for the application process. The composition 22 may be applied using any conventional process, including knife over roll coating, or roll coating, either in a continuous coverage or a patterned coverage. Printing applications are other suitable application techniques, including gravure printing, screen, and jet printing. The binder composition 22 may also be applied to the substrate using a spray application.

In another embodiment, the absorbent binder composition 22 may be prepared using a continuous process wherein the polymerization and/or neutralization reaction is carried out in a suitable reactor that conveys the resulting binder composition, upon completion of the polymerization reaction, directly to an apparatus for applying the absorbent binder composition onto the sheets 12, 14. Such a continuous process may be desirable where conditions, such as high heat, may cause premature crosslinking of the binder composition that would hinder application of the absorbent binder composition onto the substrate.

The absorbent binder composition 22, particularly the crosslinked water soluble polymer component, is described in detail in co-pending and commonly owned U.S. patent application Ser. No. 10/427,809 entitled ABSORBENT BINDER COMPOSITION AND METHOD OF MAKING IT, and Ser. No. 10/427,808 entitled ABSORBENT ARTICLE WITH SELF-FORMING ABSORBENT BINDER LAYER. These applications are incorporated herein by reference in their entirety for all purposes. The composition 22 is also described in detail below.

The absorbent binder composition 22 includes a hydrophilic polymer which is capable of post-application, moisture-induced crosslinking, is relatively inexpensive to produce, and has a high level of flexibility. The flexible nature of the absorbent binder is useful when the binder is employed in personal care absorbent articles, particularly interlabial absorbent articles 10 according to the invention.

The absorbent binder composition 22 includes about 15 to about 99.9% by mass of monoethylenically unsaturated polymer units. Suitable monoethylenically unsaturated polymers include without limitation carboxylic acid, sulphonic acid, phosphonic acid, and salts of the foregoing. Additional examples are provided in greater detail in the co-pending patent applications referenced above and incorporated herein.

The absorbent binder composition also includes about 0.1 to about 20% by mass of polyacrylate ester units, such as acrylate and/or methacrylate ester units, that include an alkoxysilane functionality. The acrylate and/or methacrylate ester units are copolymerized with the monoethylenically unsaturated monomer units. In particular, the absorbent binder composition may include about 0.5 to about 15% by mass of the acrylate and/or methacrylate ester units, for instance about 1.0 to about 10% by mass, for instance about 1.5 to about 5.5% by mass. The alkoxysilane functionality is a functional group or moiety that reacts with water to form a silanol group which condenses to form a crosslinked polymer. One suitable alkoxysilane group is a trialkoxy silane.

The term "monomer(s)" as used herein includes monomers, oligomers, polymers, mixtures of monomers, oligomers and/or polymers, and any other reactive chemical species which is capable of co-polymerization with monoethylenically unsaturated carboxylic, sulphonic or phosphoric acid or salts thereof. Ethylenically unsaturated monomers containing a trialkoxy silane functional group are appropriate for this invention and are desired. Suitable ethylenically unsaturated monomers include acrylates and methacrylates. A particularly ethylenically unsaturated monomer containing a trialkoxy silane functional group is methacryloxypropyl trimethoxy silane, commercially available from Dow Corning, having offices in Midland, Mich., under the trade designation Z-6030 Silane. Other suitable ethylenically unsaturated monomers containing a trialkoxy silane functional group include, but are not limited to, methacryloxyethyl trimethoxy silane, methacryloxypropyl triethoxy silane, methacryloxypropyl tripropoxy silane, acryloxypropylmethyl dimethoxy silane, 3-acryloxypropyl trimethoxy silane, 3-methacryloxypropylmethyl diethoxy silane, 3-methacryloxypropylmethyl dimethoxy silane, and 3-methacryloxypropyl tris(methoxyethoxy) silane. However, it is contemplated that a wide range of vinyl and acrylic monomers having trialkoxy silane functional groups or a moiety that reacts easily with water to form a silanol group, such as a chlorosilane or an acetoxysilane, provide the desired effects are effective monomers for copolymerization in accordance with the present invention.

The absorbent binder composition also includes about 0.1 to about 75% by mass polyolefin glycol and/or polyolefin oxide units, suitably about 5 to about 75% by mass, particularly about 10 to about 60% by mass, particularly about 20 to about 50% by mass, particularly about 30 to about 40% by mass. The polyolefin glycol or oxide may be a glycol or oxide of an olefin polymer having about 2 to about 4 carbon atoms. The polyolefin glycol and/or oxide may be graft polymerized with the acrylate or methacrylate ester to form a graft copolymer. The polyolefin glycol and/or oxide may be a homopolymer or copolymer. The polyolefin glycol and/or oxide may be a block copolymer including olefin glycol or oxide units having different numbers of carbon atoms, for instance, block copolymers of ethylene oxide and propylene oxide. The polyolefin glycol and/or oxide provides the absorbent binder composition with enhanced flexibility. Thus, the absorbent binder composition has enhanced adhesion in a wet condition, absorbency, and flexibility.

Polyethylene glycol, polyethylene oxide, polypropylene glycol and polypropylene oxide are examples of suitable polymer units. The polyolefin glycol and/or polyolefin oxide may include on average about 30 to about 15,000 glycol and/or oxide units per molecule. The weight average molecular weight of polyolefin glycol units may range from about 200 to about 8000. When polyolefin oxide units are employed, they may have a weight average molecular weight of about 100,000 to about 600,000.

Polyolefin glycols and polyolefin oxides are commercially available, and are common. To prepare the absorbent binder composition of the invention, a pre-formed polyolefin glycol and/or oxide may be dissolved or dispersed in a reaction vessel which includes an aqueous solvent or carrier, an organic solvent or carrier such as ethanol, or a miscible combination of aqueous and organic solvent or carrier. The monomers used to form the monoethylenically unsaturated polymer units and the polyacrylate ester units are added to the solution and polymerized using a template polymerization process in which the polyolefin glycol or oxide serves as a template polymer. Before initiation, the polar groups of the monomers, for instance the acid groups of acrylic acid, are attracted to the polyolefin glycol and/or polyolefin oxide through hydrogen bonding. The steric alignment of the monomers, with the polyolefin glycol and/or oxide serving as backbone, aids in the polymerization and typically increases the chain length of the polymerizing unit. During the polymerization, radical polymerizing chains may become attached to the template polymer, resulting in grafting of polyolefin glycol and/or oxide to the copolymer being formed. However, this graft polymerization need not occur. The resulting absorbent binder composition includes the polyolefin glycol and/or oxide attached to, and/or blended with, the copolymer of the monoethylenically unsaturated polymer units and the acrylate or methacrylate ester units that include the alkoxysilane functionality.

The absorbent binder composition can be prepared using a template polymerization process by which the monoethylenically unsaturated polymer and acrylate or methacrylate ester are polymerized in the presence of a pre-formed template polymer, which is the polyolefin glycol and/or polyolefin oxide. The polymerization can be carried out by reacting two different monoethylenically unsaturated monomers, one of which contains an alkoxysilane functionality. The polymerization may be initiated using a variety of methods, including without limitation thermal energy, ultraviolet light, and redox chemical reactions. A solution of the above ingredients may be added to an initiator solution at a temperature suitable for generating free radicals, for instance about 50 to about 90° C. An initiator may be prepared by dissolving an initiator in an organic or aqueous solvent. A suitable class of initiators are organic peroxides and azo compounds, with benzoyl peroxide and azobisisobutylnitrile (ABN) as examples. The initiator generates free radicals to cause copolymerization of the monomers. In one embodiment, the polymerization reaction is carried out in an organic solvent such as ethanol. The polymerization may also occur in an aqueous solution, or in a combined aqueous and organic solvent.

The polyolefin glycol and/or oxide may or may not be graft polymerized onto the acrylate or methacrylate units during the polymerization process. The resulting absorbent binder composition may contain the polyolefin glycol and/or oxide as a separate component, or as part of the copolymer, or a combination of both.

The resulting polymer has latent moisture-induced crosslinking capability due to the alkoxysilane functionality. This polymer may be applied, in a flowable state, to a substrate or other end use application. Moisture-induced crosslinking may be accomplished through hydrolysis of the alkoxysilane and subsequent condensation upon removal of the solvent from the substrate, either by evaporation of the solvent from the substrate or using any other effective technique. Alternatively, the hydrolysis of the alkoxysilane and subsequent condensation may occur after solvent removal by exposure of the coating to moisture in ambient air.

In one embodiment, the absorbent binder composition is made by combining a first aqueous monomer solution including a reducing polymerization initiator with a second aqueous monomer solution including an oxidizing polymerization initiator, wherein the initiators react to form a binder composition. The first aqueous monomer solution further includes a monoethylenically unsaturated monomer and an ethylenically unsaturated monomer that contains an alkoxysilane functionality. The second aqueous monomer solution includes a monoethylenically unsaturated monomer. One or both solutions may include the polyolefin glycol and/or polyolefin oxide template polymer. Suitably, the binder composition is formed in about 100 minutes or less, or about 60 minutes or less, desirably in about 30 minutes or less, or about 15 minutes or less, or about 10 minutes or less.

The pH of the first and/or second aqueous monomer solution is adjusted to about 4.5 to about 8, suitably about 5.5 to about 7.0. The pH of the first aqueous solution may be adjusted prior to the addition of the ethylenically unsaturated monomer. Desirably, the pH of the first aqueous monomer solution is adjusted prior to the addition of the reducing polymerization initiator. The pH of the second aqueous solution may be adjusted prior to the addition of the oxidizing polymerization initiator. Alternatively, the pH of the combined first and second aqueous monomer solutions may be adjusted to about 4.5 to about 8, suitably about 5.5 to about 7.0. If desired, the pH may be increased after polymerization is complete, by addition of a suitable basic solution. The extent of neutralization can be used to adjust the properties of the coating. Greater neutralization of the acid functional components generally enhances absorbent capacity, while greater acid functionality generally enhances adhesion.

The amounts of the polymerization ingredients added to the first and second aqueous solutions are selected so as to produce the absorbent binder composition having the composition described above.

In one embodiment, a surfactant may be added to the first and/or second aqueous monomer solution to disperse the ethylenically unsaturated monomer. One surfactant suitable for use in the present invention is a dioctyl sodium sulfosuccinate available under the trademark AEROSOL OT from Cytec Industries, Inc. of Paterson, N.J.

The first aqueous monomer solution further includes a reducing polymerization initiator. Suitable reducing polymerization initiators include, but are not limited to, ascorbic acid, alkali metal sulfites, alkali metal bisulfites, ammonium sulfite, ammonium bisulfite, alkali metal hydrogen sulfite, ferrous metal salts such as ferrous sulfates, sugars, aldehydes, primary and secondary alcohols, and combinations thereof. In one embodiment, the reducing polymerization initiator includes ascorbic acid.

The second aqueous monomer solution further includes an oxidizing polymerization initiator. Suitable oxidizing initiators include, but are not limited to, hydrogen peroxide, alkali metal persulfates, ammonium persulfate, alkylhydroperoxides, peresters, diacryl peroxides, silver salts, and combinations thereof. In one embodiment, the oxidizing polymerization initiator includes hydrogen peroxide.

Generally, when the first aqueous monomer solution is combined with the second aqueous monomer solution the reducing polymerization initiator reacts with the oxidizing polymerization initiator, e.g. a redox reaction, thereby initiating a polymerization reaction to form a binder composition including a monoethylenically unsaturated monomer and an ethylenically unsaturated monomer that has post-application, moisture-induced crosslinking capability.

The binder composition may be applied to a substrate and subsequently dried to form a cast film. Once the binder composition is applied to the substrate, crosslinking can be moisture-induced by hydrolysis and condensation of alkoxysilanes. For example, crosslinking of the binder composition can be induced by concentrating the binder composition on the substrate through the removal of the water to promote condensation of silanols generated by hydrolysis of alkoxysilanes. Typically, crosslinking begins at a solution concentration of about 30 percent or greater by weight binder composition. Furthermore, if the substrate material has hydroxyl group functionality on its surface, then the silanols within the binder composition may react with the hydroxyl groups to form a covalent bond between the binder and the hydroxyl-containing surface. Non-limiting examples of substrates with hydroxyl surface functionality include glass, sand and cellulose.

One advantage of the absorbent binder composition of the invention is that it provides a water-soluble ionic polymer capable of sufficient spontaneous crosslinking within about 10 minutes, at a temperature not more than about 120° C., to reach an absorbent capacity of at least one gram of fluid per gram of absorbent binder composition, suitably at least three grams of fluid per gram of absorbent binder composition, using the centrifuge retention capacity test described herein. The term "spontaneous" crosslinking refers to crosslinking which occurs without radiation, catalysis, or any other inducement other than the specified temperature of not more than about 120° C., suitably not more than about 100° C. Eliminating the need for radiative crosslinking provides a significant processing advantage. The crosslinking at temperatures not more than about 120° C., suitably not more than about 100° C., permits the absorbent binder composition to be applied to a substrate such as an absorbent article, and then crosslinked without degrading or damaging the substrate. The crosslinking occurs within about 10 minutes, suitably within about 8 minutes, particularly within about 6 minutes provides an efficient, commercially feasible, cost-effective crosslinking process. The ionic polymer may bear a positive charge, a negative charge, or a combination of both, and should have an ionic unit content of about 15 mole percent or greater. The ionic polymer may include a variety of monomer units described above, and suitably contains a carboxyl group-containing unit or a quaternary ammonium-containing unit.

The absorbent binder composition 22 desirably provides the article 10 with sufficient capacity to absorb and retain the intended amount and type of bodily exudate(s). The composition 22 can have an absorbent capacity of at least about 1 g/g. One of skill in the art will readily realize that the absorbent capacity of the article 10 can also be significantly increased by the addition of a superabsorbent polymer to the composition 22 or within the article. For example, a superabsorbent coating may be applied to either or both of the sheets 12, 14. Superabsorbent coatings, particles, and the like, for use in personal care absorbent articles are well known by those skilled in the art.

It should thus be recognized that the absorbent capacity of the interlabial absorbent article 10 may be a sole function of the capacity of the absorbent binder composition 22, or may be a function of a combination of the composition 22 and a supplemental absorbent material, such as a superabsorbent or supplemental absorbent layer 18. A suitable combination to achieve a desired absorbent capacity may be empirically determined with relative ease by those skilled in the art.

As described, the absorbent crosslinked polymer component of the binder composition 22 is generally water swellable (and may be partially or fully soluble) and, alone, would not sufficiently adhere the components of the article 10 together for the desired time of at least about two hours after being flushed. In this regard, a polymer dispersion is added to the composition 22 prior to crosslinking in an amount such that the composition 22 maintains structural integrity of the article 10 for a time period of at least about two hours after the article is immersed in water by being flushed. The polymer dispersion functions in essence as a time-delay agent in that it holds the components together for at least about two hours, but allows the components to eventually separate and disperse. Desirably, the polymer dispersion is present in an amount such that the article looses structural integrity within about 24–72 hours after immersion. The polymer dispersion may be one or a combination of widely recognized binding agents, such as a latex, cellulose ester, and the like. For example, the polymer dispersion may be RHOPLEX B-15R acrylic dispersion from Rohm and Haas Co. of Philadelphia, Pa. The polymer dispersion may be mixed homogeneously with the composition 22 so as to provide the composition with a "slow" debondable adhesive characteristic. The amount of polymer dispersion to be added will depend on a variety of factors, including size and shape of the article 10, absorbent capacity of the article, types of materials used, etc., and can be readily empirically determined through routine experimentation for a desired configuration of article 10.

The absorbent binder composition 22 may be applied between the cover sheet 12 and baffle 14 in any number of patterns. For example, referring to FIG. 1, the composition 22 is applied as a generally uniform continuous coating between the sheets generally to the circumferential edges 16 of the sheets. In this embodiment, the composition 22 is essentially the sole adhering or binding component and forms a complete seal around the circumference of the article 10. Alternatively, a supplemental seal may be provided around the circumference of the article 10. For example, referring to FIG. 3, a supplemental seal 34 may be provided in the edge region 26 around the article 10. This supplement seal 34 may be any one or combination of conventional seals, including adhesive, thermal, ultrasonic, and so forth. Such sealing processes are well known to those skilled in the art. Care should be taken to ensure that any supplemental bond or seal 34 is not so strong that it prevents the article from eventually dispersing, preferably within bout 24 to about 72 hours after immersion.

Figures 5, 6:
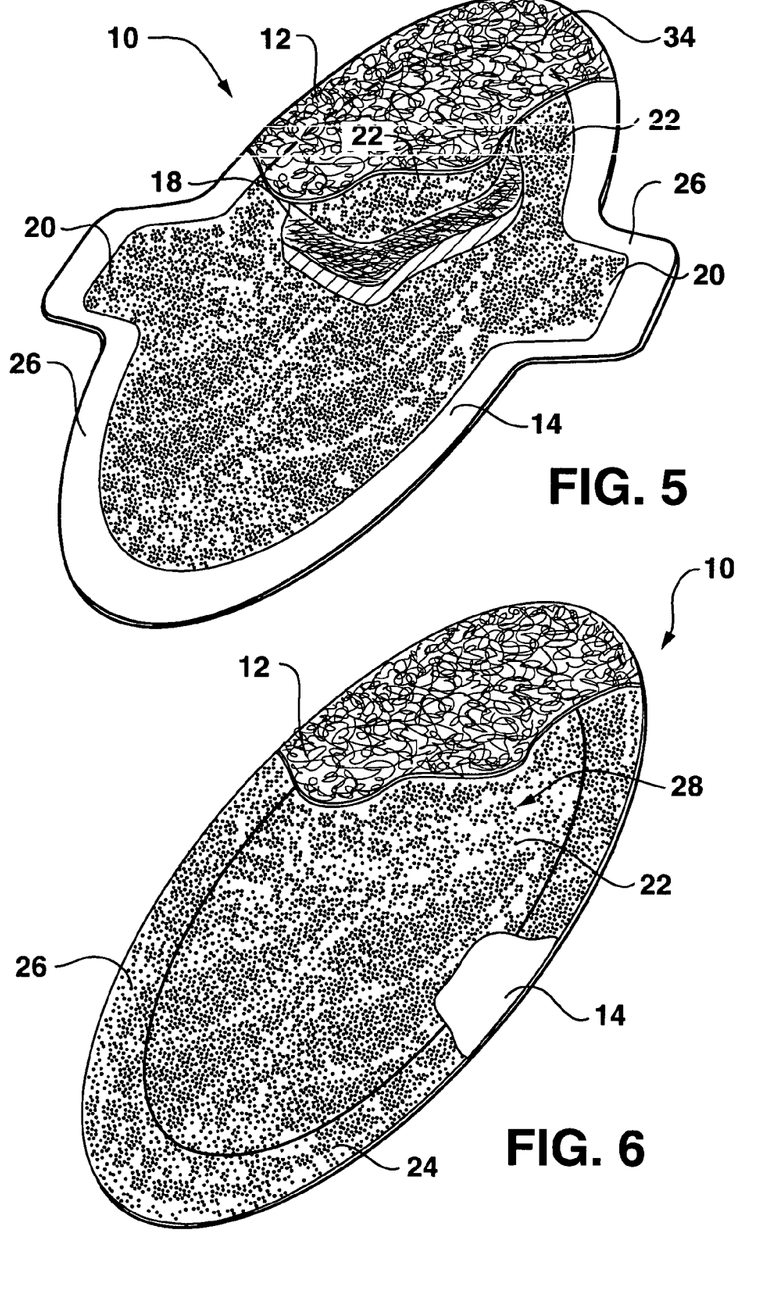
FIG. 5 is a partial cut-away view of an alternate embodiment of an interlabial absorbent article in accordance with the invention.
FIG. 6 is a partial cut-away view of an alternate embodiment of an interlabial absorbent article in accordance with the invention.

With the embodiment of FIG. 5, the absorbent binder composition 22 is applied to the baffle 14 generally in a central region bordered by circumferential edge regions 26. The edge regions 26 are uncoated or coated with a different composition 22 such that the peripheral area of the pad is more tightly bonded. With this embodiment, a conventional seal, such as a thermal or ultrasonic bond, would be applied in the edge regions to adhere the cover sheet 12 to the baffle 14. The composition 22 would adhere the sheets 12,14 together in the central region 28.

It is also within the scope and spirit of the invention to utilize different absorbent binder compositions within the same article. For example, with the embodiment of FIG. 6, the central region has a layer of a first absorbent binder composition 22 and the edge regions 26 have a layer of a second absorbent binder composition 24. The second composition 24 may contain a greater percentage (i.e., by weight, volume, or concentration) of the polymer dispersion as compared to the composition 22 such that the composition 24 has increased adhering capability as compared to the composition 22.

Still referring to FIG. 6, it should be further understood that the composition 22 in the central region 28 may contain a greater amount (weight, volume, or concentration) percentage of the absorbent polymer component as compared to the composition 24 in the edge regions 26. Thus, the central region 28 has an enhanced absorbent capacity as compared to the edge regions 26. The two compositions 22, 24 may have the same amount of the polymer dispersion.

Figure 7:
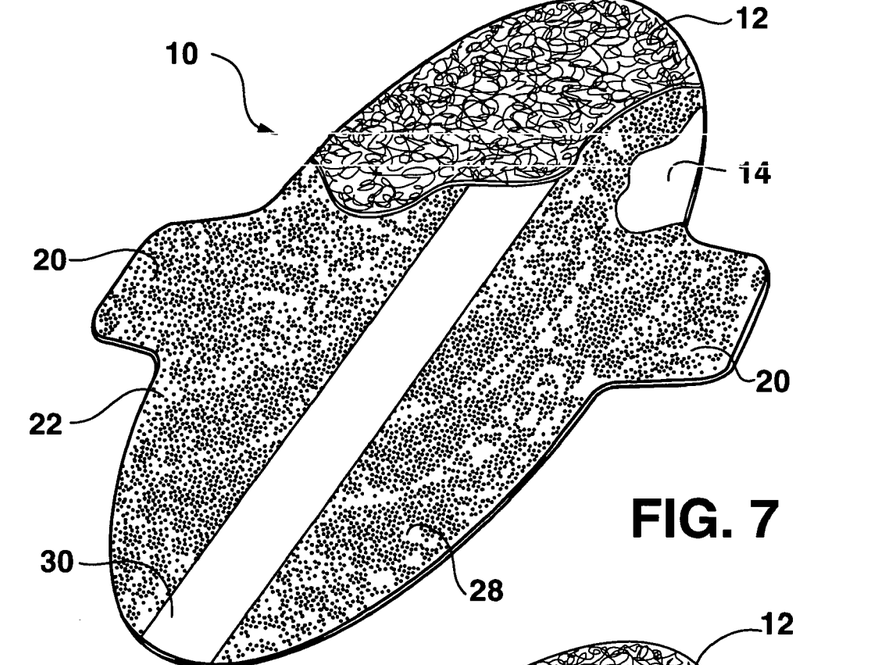
FIG. 7 is a partial cut-away view of an alternate embodiment of an interlabial absorbent article in accordance with the invention.

FIG. 7 illustrates another embodiment wherein a central longitudinally disposed region 30 is uncoated with the composition 22. Alternatively, the region 30 may be coated with a lesser amount of the composition 22 as compared to other regions. The region 30 is generally coincident with a fold line 32 (see FIG. 1) about which the article 10 may be folded by the wearer for insertion. Although the composition 22 is relatively flexible, the uncoated region 30 enhances foldability of the article. The region 30 may or may not extend to the edges of the article 10.

Figure 8:
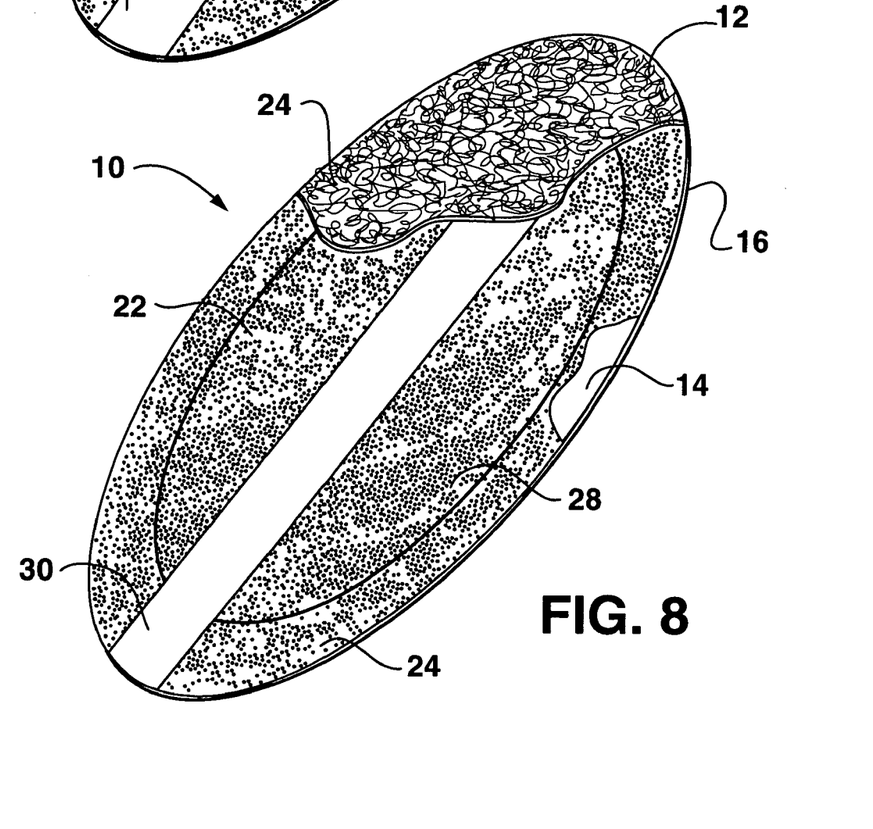
FIG. 8 is a partial cut-away view of an alternate embodiment of an interlabial absorbent article in accordance with the invention.

FIG. 8 is an embodiment that incorporates the uncoated region 30 of FIG. 7 and the differing compositions 22, 24 as discussed above with respect to FIG. 6.

Test Method for Determining Absorbent Capacity

As used herein, the Centrifuge Retention Capacity (CRC) is a measure of the absorbent capacity of the superabsorbent material retained after being subjected to centrifugation under controlled conditions. The CRC can be measured by placing a sample of the material to be tested into a water-permeable bag which will contain the sample while allowing the test solution (0.9 weight percent NaCl solution) to be freely absorbed by the sample. A heat-sealable tea bag material (available from Dexter Nonwovens of Windsor Locks, Conn., U.S.A., as item #11697) works well for most applications. The bag is formed by folding a 5-inch by 3-inch sample of the bag material in half and heat sealing two of the open edges to form a 2.5-inch by 3-inch rectangular pouch. The heat seals should be about 0.25 inch inside the edge of the material. After the sample is placed in the pouch, the remaining open edge of the pouch is also heat-sealed. Empty bags are also made to be tested with the sample bags as controls. A sample size is chosen such that the teabag does not restrict the swelling of the material, generally with dimensions smaller than the sealed bag area (about 2-inch by 2.5 inch). Three sample bags are tested for each material.

The sealed bags are submerged in a pan of 0.9% wt NaCl solution. After wetting, the samples remain in the solution for 60 minutes, at which time they are removed from the solution and temporarily laid on a non-absorbent flat surface.

The wet bags are then placed into the basket of a suitable centrifuge capable of subjecting the samples to a g-force of 350. (A suitable centrifuge is a Heraeus LABOFUGE 400, Heraeus Instruments, part number 75008157, available from Heraeus Infosystems GmbH, Hanau, Germany). The bags are centrifuged at a target of 1600 rpm, but within the range of 1500–1900 rpm, for 3 minutes (target g-force of 350). The bags are removed and weighed. The amount of fluid absorbed and retained by the material, taking into account the fluid retained by the bag material alone, is the Centrifugal Retention Capacity of the material, expressed as grams of fluid per gram of material.

Water Dispersion Test

This protocol measures the ability of absorbent articles to disperse or fall apart upon contact with water, such as by being flushed. A similar suitable water dispersion test in described in U.S. Pat. No. 6,270,486 B1 incorporated herein by reference for all purposes.

The water dispersion test is described below:

Apparatus:

Shaker (Junior Orbit Shaker available from Lab Line Instruments)

Thermometer (30 to 120 degrees Fahrenheit, with 1 degree divisions)

Timer (Digital Stopwatch)

Jar with Lid (16 oz. glass jar with lid)

Conditioned Room (Temperature and humidity should be controlled to remain within the following limits: Temperature-73 F, Humidity-50% RH)

Test Set-UP:

1. Fill the glass jar with 300 ml of 73 F tap water.
2. Set the speed on the Junior Orbit Shaker to 250 rpm.

Procedure:

1. Hold a product sample 3 to 4 inches above the surface of the water in the jar. Gently drop the sample onto the water surface.
2. Place the lid on the jar.
3. Place the jar into the Junior Orbit Shaker such that the jar is oriented on its side.
4. Start the Junior Orbit shaker with the on/off switch, starting the timer when the shaker is turned on.
5. Record the time required until the product sample separates into at least two pieces. Separation does not include disassociation of a few individual fibers from an otherwise intact sample. The time is the total time the sample is being shaken.
6. Repeat steps 1–5 with any additional samples.

Calculation and Reporting:

Calculate and report the mean and standard deviation of the water dispersibility time for the four samples tested.

EXAMPLE

Absorbent Binder Preparation:

A first solution (Solution No. 1) was prepared as follows: To 14.4 grams (0.20 moles) of acrylic acid in a 200 ml beaker was added 33.3 grams of a 18% aqueous solution of polyethylene glycol 8000, followed by a solution of 3.2 grams of sodium hydroxide in 21.4 grams of distilled water. Then, 0.18 grams (concentration of $1.02 \times 10^{-3}$ moles) of ascorbic acid was added to the solution. This mixture was stirred with a magnetic stir bar at about 60 rpm in a bath of water at about 23° C. until the ascorbic acid was dissolved and the mixture cooled to 23° C.

A second solution (Solution No. 2) was prepared in the following manner: To 14.4 grams (0.20 moles) of acrylic acid, in a 300 ml beaker was added to 33.3 grams of a 18% aqueous solution of polyethylene glycol 8000 (mol. wt.=8000) followed by a solution of 3.2 grams of sodium hydroxide in 21.4 grams of distilled water, 0.57 ml of 30% aqueous hydrogen peroxide and 1.0 ml ($5.42 \times 10^{-3}$ moles) of 3-(trimethoxysilyl)propyl methacrylate. The ingredients were added with stirring to produce a clear solution. This mixture was stirred with a magnetic stir bar at about 60 rpm in a bath of water at about 23° C. to provide a clear solution cooled to 23° C.

A third solution was prepared by dissolving 8 grams (0.20 moles) sodium hydroxide in 160 grams of distilled water.

Solution No. 2 was added to Solution No. 1 while stirring with a magnetic stir bar at about 60 rpm. A thermocouple was used to monitor the temperature and observe the reaction exotherm. The polymerization reaction began within about 30 seconds of mixing as the temperature rose from 23° C. to 40° C. A maximum temperature of about 70° C. was observed after three minutes of mixing the two solutions. The polymerization transformed the combined solutions into a soft gel. The gel was cut into pieces of about 1 cm³ and added to the solution of 8 grams (0.20 moles) sodium hydroxide in 160 grams of distilled water. With continued stirring, aided by an Ultraturax homogenizer at 11,000 rpm, the soft gel became a viscous translucent solution.

Acrylic polymer dispersion (RHOPLEX B-15R available from Rohm and Haas Company, Philadelphia, Pa.) was diluted with deionized water to 10% (w/w) dispersion.

Blends of the absorbent polymer and the acrylic dispersion were prepared by mixing the 10% solution and dispersion solution in various proportions as listed in the Table below. 15 grams of each blend was poured into a polystyrene weighing dish and allowed to dry in a laboratory hood for 16 hours. The resultant films were tested for absorbent capacity using the Centrifuge Retention Capacity (CRC) test described below. The compositions and the absorbent capacity results are listed in the Table:

TABLE

| Blend | Grams Absorbent polymer solution | Grams RHOPLX B15-R dispersion | Absorbent capacity of cast films (g/g) |
|---|---|---|---|
| 1 | 70 | 30 | 4.7 |
| 2 | 50 | 50 | 5.6 |
| 3 | 30 | 70 | 1.8 |
| 4 | 100 | 0 | 7.1 |
| 5 | 4.5 | 145.5 | — |
| 6 | 3.0 | 147 | — |
| 7 | 5 | 95 grams Noveon Hystretch ® Latex V29* | 0.9 |

*Noveon Hystretch ® Latex V29 ®® is available from Noveon, Inc., Cleveland, Ohio.

Sample Preparation:

Test Samples were made by applying about 5 g of one of the blends above to a 2.5 inch by 2.5 inch polyethylene baffle film material and spreading the blend across the surface by hand with a plastic spatula. An absorbent core (either Basotect® foam or a cotton/rayon blend fiber structure) was cut to 2 inch by 2 inch and placed on top of the baffle film. A 2.5 inch by 2.5 inch apertured cover sheet was placed on top of the absorbent core. All four sides of the cover sheet were pressed down onto the baffle and held together by the tackiness of the absorbent binder composition. The samples were placed in a Constant Temperature Oven, Model DK-63, available from Scientific Products, at 80° C. until the samples were dry. The dried binder composition bound the baffle to the cover sheet, thus holding the pad together.

Certain of the samples were tested without bonding. Other samples were further ultrasonically bonded along each of the four edges of the pad, as described below.

Dispersion Tests Results:

The prepared samples were tested using the Dispersion Test described above, with the following results:

Blends 1 and 4:

These blends were not specifically tested because they contained higher levels of the absorbent polymer than blend 2, which dispersed quickly. It was anticipated that the samples made with blends 1 and 4 would disperse at least as quickly as the samples made with Blend 2.

Blend 2:

For all samples, the baffle and cover sheet separated in less than 5 minutes after transfer to the container.

Blend 3:

For all samples, the baffle and cover sheet separated in less than 5 minutes after transfer to the container. Samples bonded with blend 3 and also ultrasonically bonded with one bond along each of the four sides (after oven drying) stayed together for about 15 minutes after transfer to the container.

Blend 5:

Four different samples were made with Blend 5.

Sample 5A:

This sample was made as described above with Basotect® foam (available from BASF Corp.) as the absorbent core. The foam may or may not be treated with a surfactant. No additional ultrasonic bonding was done. The baffle and cover sheet separated after 36 minutes from transfer to the container. The foam and baffle stayed together for the length of the observation time (4 hours).

Sample 5B:

This sample was the same as Sample 5A with one ultrasonic seal along each of the four sides. The bonds were made with a Branson 900 Series ultrasonic plunge bonder with a weld time of 1.9 seconds at a pressure of 490 pounds per square inch. At 3.5 hours after transfer to the container, the baffle partially separated from the cover sheet. The baffle remained partially attached to the cover for the length of the test (4 hours).

Sample 5C:

This sample was the same as Sample 5B with two ultrasonic seals along each of the four sides of the pad. At 4 hours, there was no sign of separation of the baffle from the cover sheet.

Sample 5D:

This sample was the same as Sample 5C with a rayon/cotton blend used as the absorbent core. At 4 hours, there was no sign of separation of the baffle from the cover sheet.

Samples were also tested where the baffle film was ultrasonically bonded to the cover sheet without application of the absorbent binder composition. These samples failed immediately (complete separation of the baffle from the cover sheet) after transfer to the container.

Sample 6:

This sample was made as described above with Basotect® foam as the absorbent core material. No additional ultrasonic bonding was done. The baffle and cover sheet separated after about 1 hour and 15 minutes from transfer to the container.

Sample 7:

This sample was made as described above with Basotect® foam as the absorbent core material. No additional bonding was done. The baffle and cover sheet separated after 2 hours and 44 minutes from transfer to the container.

CONCLUSION

The samples and tests described above demonstrate that the amounts of absorbent polymer and polymer dispersion present in the absorbent polymer composition may be varied to achieve different degrees of adhesion and absorbent capacity. The use of ultrasonic bonds alone was insufficient in holding the baffle and cover together. However, the use of ultrasonic bonds as a supplement to the absorbent binder composition was satisfactory. Samples were also tested wherein solely the absorbent binder composition held the article together for two hours. It is believed that one skilled in the art may readily empirically determine the proper ratio and concentrations of absorbent polymer and polymer dispersion for an absorbent binder composition that would hold the article together for the required time period and provide the desired degree of absorption capacity.

It should be appreciated by those skilled in the art that various modifications and variations may be made to the embodiments of the invention illustrated or described herein without departing from the scope and spirit of the invention as set forth in the appended claims and their equivalents.

What is claimed is:

1. An interlabial absorbent article configured for disposition primarily within the vestibule of a female wearer, comprising:
   a generally liquid permeable cover sheet;
   a generally liquid impermeable baffle;
   a water soluble flexible absorbent binder composition applied between said cover sheet and said baffle;
   said absorbent binder composition adhering said cover sheet to said baffle;
   a supplemental seal around the circumference of the article; and
   said absorbent binder composition comprising a crosslinked absorbent polymer and a polymer dispersion added in an amount and at a location so as to maintain structural integrity of said article for a time period of at least four hours after said article is immersed in water by being flushed.

2. The interlabial absorbent article as in claim 1, wherein said supplemental seal is configured and said polymer dispersion is present in an amount such that said article does not lose structural integrity until between about 24–72 hours after immersion.

3. The interlabial absorbent article as in claim 1, wherein said absorbent polymer comprises a water-soluble ionic polymer capable of sufficient non-radiative crosslinking within about 10 minutes at a temperature not more than about 120° C., to reach an absorbent capacity of at least one gram per gram using the centrifuge retention capacity test.

4. An interlabial absorbent article configured for disposition primarily within the vestibule of a female wearer, comprising:
   a generally liquid permeable cover sheet;
   a generally liquid impermeable baffle;
   a water soluble flexible absorbent binder composition applied between said cover sheet and said baffle;
   said absorbent binder composition adhering said cover sheet to said baffle;
   said absorbent binder composition comprising a crosslinked absorbent polymer and a polymer dispersion added in an amount and at a location so as to maintain structural integrity of said article for a time period of at least two hours after said article is immersed in water by being flushed;
   wherein said absorbent polymer comprises a water-soluble ionic polymer capable of sufficient non-radiative crosslinking within about 10 minutes at a temperature not more than about 120° C., to reach an absorbent capacity of at least one gram per gram using the centrifuge retention capacity test; and
   wherein said absorbent polymer comprises about 15 to about 99.9% by mass monoethylenically unsaturated polymer units, about 0.1 to about 20% by mass ester units selected from the group consisting of acrylate and methacrylate ester units that include an alkoxysilane functionality, and about 0.1 to about 75% by mass of units selected from the group consisting of polyolefin glycol and polyolefin oxide units.

5. The interlabial absorbent article as in claim 1, wherein said polymer dispersion comprises at least one of a latex and a cellulose ester.

6. The interlabial absorbent article as in claim 1, wherein said absorbent binder composition provides said article's sole absorbent capacity.

7. The interlabial absorbent article as in claim 1, further comprising a supplemental absorbent material layer provided between said cover sheet and said baffle.

8. The interlabial absorbent article as in claim 1, comprising regions coated with different variations of said absorbent binder composition.

9. The interlabial absorbent article as in claim 8, wherein said absorbent binder composition in regions generally adjacent circumferential edges of said cover sheet and said baffle comprises an increased amount of said polymer dispersion so as to define an enhanced circumferential seal region.

10. The interlabial absorbent article as in claim 8, wherein said absorbent binder composition in a central region of said cover sheet and said baffle comprises an increased amount of said absorbent polymer.

11. The interlabial absorbent article as in claim 1, comprising a generally central longitudinally disposed region between said cover sheet and said top sheet having a lesser or no amount of said absorbent binder composition and defining a weakened area of said article.

12. The interlabial absorbent article as in claim 1, comprising a generally central longitudinally disposed region between said cover sheet and said top sheet uncoated with said absorbent binder composition, said uncoated region defining a fold line for said article, said polymer dispersion being present in circumferential edge regions in an amount greater than in a generally central longitudinally disposed region bordered by said circumferential edge regions.

13. The interlabial absorbent article as in claim 1, further comprising a second supplemental seal between said cover sheet and said baffle.

14. The interlabial absorbent article as in claim 13, wherein said second supplemental seal comprises any combination of thermal, microwave, ultrasonic, mechanical, cohesive, and adhesive seal.

15. The interlabial absorbent article as in claim 1, further comprising a supplemental absorbent material layer provided between said cover sheet and said baffle, said supplemental absorbent material layer coated with said absorbent binder composition.

16. The interlabial absorbent article as in claim 1, wherein said cover sheet comprises a coating of said absorbent binder composition on an outer surface thereof to enhance hydrosity of said cover sheet.

17. A method for forming an interlabial absorbent article that maintains its structural intearity in water for at least about four hours, said method comprising:
    providing a cover sheet and a baffle;
    applying a coating of a water soluble absorbent binder composition to at least one of the cover sheet and the baffle;
    crosslinking the absorbent binder composition to provide a flexible absorbent binder layer adhered to both the cover sheet and the baffle; and
    providing a supplemental seal around the circumference of the article and providing the absorbent binder composition with a polymer dispersion in an amount so as to maintain structural integrity of said article for a time period of at least four hours after said article is immersed in water by being flushed.

18. The method as in claim 17, further comprising providing a supplemental absorbent material layer between the cover sheet and the baffle.

19. The method as in claim 17, comprising applying a greater concentration of the polymer dispersion around a circumference edge region of the cover sheet and the baffle to provide an enhanced circumferential seal region.

20. The method as in claim 17, comprising applying an additional seal between the cover sheet and the baffle.

21. The method as in claim 20, wherein the additional seal is any combination of a thermal, adhesive, microwave, mechanical, and ultrasonic seal.

22. The method as in claim 17, comprising defining a generally centrally disposed longitudinal region between the cover sheet and the baffle that is uncoated with the absorbent binder composition, the uncoated region defining a fold line for the article.

* * * * *